United States Patent [19]

Rios

[11] Patent Number: 4,568,178
[45] Date of Patent: Feb. 4, 1986

[54] FINGERPRINT PHOTOCOPY SYSTEM

[76] Inventor: Arturo M. Rios, P.O. Box 10069, St. Petersburg, Fla. 33516

[21] Appl. No.: 465,811

[22] Filed: Apr. 17, 1984

[51] Int. Cl.⁴ .............................................. G03B 27/52
[52] U.S. Cl. ........................................ 355/40; 354/62
[58] Field of Search .................... 354/62, 109; 355/40, 355/47, 49

[56] References Cited

U.S. PATENT DOCUMENTS 3,529,520  9/1970  Thiebault .............................. 354/62
3,906,520  9/1975  Phillips .................................. 354/62

Primary Examiner—Richard A. Wintercorn
Attorney, Agent, or Firm—L. Lawton Rogers, III

[57] ABSTRACT

The disclosed apparatus is an electro-optical fingerprint photocopier to copy fingerprints of a person.

This apparatus uses a camera with one or more lenses to photocopy the impression made by the ridges on the tips of the fingers and thumbs. These impressions are useful as means for identification since no two persons have the same ridges pattern.

This apparatus also includes an automatic chart feeder, positioning and releaser, an automatic shutter control and concave-convex lenses to position the fingers. The features make possible the processing of an accurate fingerprint chart in a very short time.

The apparatus shall be especially used in the identification of persons, in the military, naval, police and immigration services, and in various commercial transactions. Also, shall be used by schools and other learning institutions for the proper identification of students.

13 Claims, 9 Drawing Figures

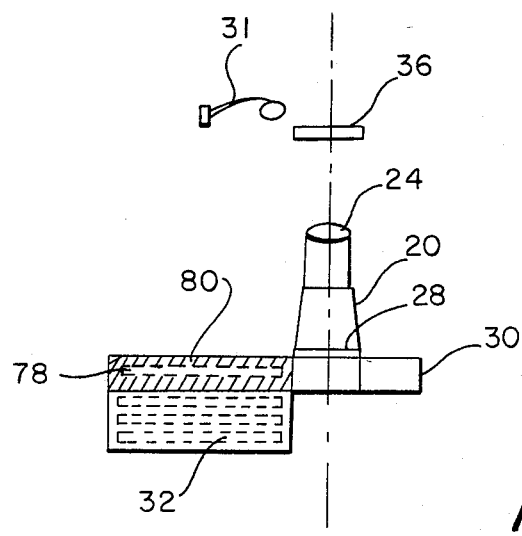
FIG. 4
FIG. 5
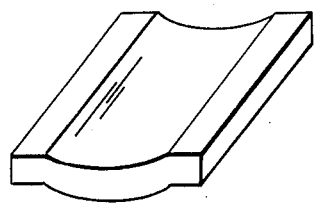
FIG. 6

FINGERPRINT PHOTOCOPY SYSTEM

BACKGROUND OF THE INVENTION

1. Field of the Invention

This invention relates to photocopiers and more particularly, to an electro-optical fingerprint photocopier that uses a macrolens camera to make accurate photocopies of the fingerprints of a person.

2. Description of the Prior Art

A conventional procedure of fingerprinting for identification purposes utilizes ink, an ink pad, a roller and a chart to get an impression of the finger ridges. This is a very slow and uncomfortable process in which both the operator and the fingerprinted person stain their hands with ink. Furthermore, the effectiveness of law enforcement organizations is significantly affected because the conventional fingerprint charts must be kept on file indefinitely for eventual reproduction on microdot applications.

There is thus a growing need for an accurate and easy-to-use fingerprint photocopier to improve and accelerate the fingerprinting procedure for identification purposes. Such an apparatus should have the capability of reducing the time to photocopy the finger impressions.

It is therefore an object of the present invention to provide an electro-optical fingerprint photocopier that accurately photocopies in color or black and white a fingerprint impression.

It is another object of the present invention to provide an electro-optical fingerprint photocopies that automatically positions a film chart during the fingerprinting process at the command of the operator thereby reducing the fingerprinting time.

It is still another object of the present invention to provide an electro-optical fingerprint photocopier that photocopies the fingerprint impressions on a film chart thereby eliminating the use of ink during fingerprinting.

It is a further object of the present invention to provide an electro-optical fingerprint photocopier that generates a fingerprint image into a flat image thereby making unnecessary to roll over the finger whose impressions are to be photocopied.

It is a further object of the present invention to provide an electro-optical fingerprint photocopier that reduces the fingerprinting time by photocopying more than one finger at the same time.

SUMMARY OF THE INVENTION

This invention accomplishes these and other objects by providing an electro-optical photocopier having an array of concave-convex lenses to position the fingers. On the concave cylindrical face of a concave-convex lens a finger is positioned so as to expose the fingerprint. The concave-convex lens generates a fingerprint flat image which image enters a macrolens camera and by means of an automatic shutter it is recorded on a flat film chart surface. This operation is repeated simultaneously for a number of fingers, in an automatic mode and at the command of the operator. Also in order to record fingerprint images at several intervals during the fingerprinting process, the film chart positions automatically so as to expose unused chart zones under the shutters about to open. A new film chart is automatically fed into the camera to start the process again. The plane lenses are used for flat fingerprinting.

These features eliminate the need for inking the fingertips of a person, the need for the person to rotate its fingers during the fingerprinting process and the continuous handling of charts during the process. All these contribute to speed up the fingerprinting process saving time to the operator and the organization as a whole.

This invention makes also easier to the operator the fingerprinting process. A group of selective keys to be used by the operator not only facilitate the control of the fingerprinting steps but also initiates the automatic operation of the shutters, and the feeding, positioning and releasing of the film charts. This invention also includes an indicator light to notify the operator that a new film stack should be provided.

When the fingerprinting process ends, a ready-to-use film chart having the recorded fingerprint impressions is released from the apparatus. A significant advantage of this chart is that later it may be recopied by ordinary means.

Furthermore, this apparatus may be arranged as a small portable unit with the finger positioning lenses, the selector keys, the film chart feeder and the film chart releaser conveniently installed at different sides of the unit. In this way the handling activity of the operator will not interfare with the hand movements of the fingerprinted person. Also, the area surrounding the finger positioning lenses is painted in a dark color so as to improve the image reproduction. In addition, a cleaning means attached to the system cleans automatically the top surface of the finger positioning lenses from impressions caused by finger contact. This cleaning operation occurs immediately after the fingerprinting of a person ends.

Other objects, features and advantages of the present invention will become apparent from the following detailed description taken in conjunction with the accompanying drawings.

BRIEF DESCRIPTION OF THE DRAWINGS

FIG. 4 is a schematic diagram of the film chart according to the invention illustrating the recording zones of the chart;

FIG. 5 is a schematic side diagram of the apparatus according to the invention illustrating the concentricity of the macrolens camera, the shutter assembly and the finger positioning assembly;

FIG. 6 is a perspective schematic diagram of a concave-convex lens according to the invention;

DETAILED DESCRIPTION OF THE PREFERRED EMBODIMENT

Figure 1:
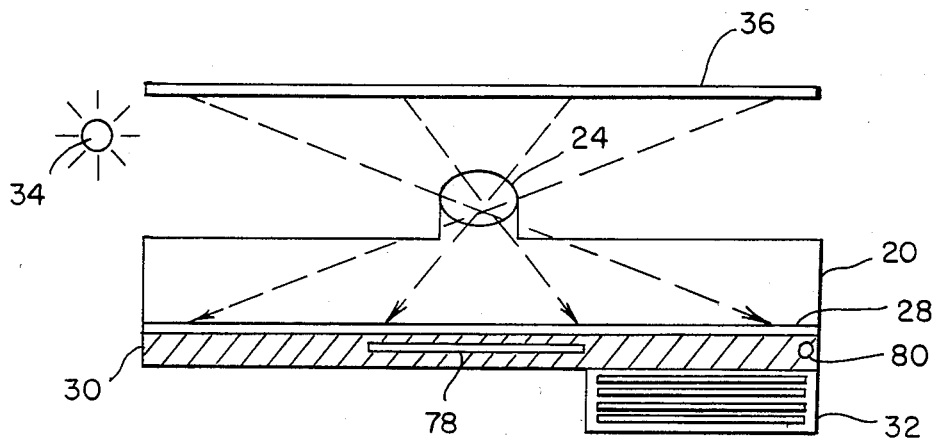
FIG. 1 is a schematic side diagram of the apparatus according to the invention illustrating a macrolens camera, the shutter assembly, the finger positioning assembly, the film chamber and the chart feeder.

Referring to FIG. 1, reference number 20 denotes the interior camera of the apparatus; 24, denotes, the lenses of the camera 20 of this embodiment; 28 denotes a shutter assembly; 30 denotes a film chamber; 32 denotes a chart feeder; 34 denotes a light source inside the apparatus; and 36 denotes a finger positioning assembly.

Figure 2:
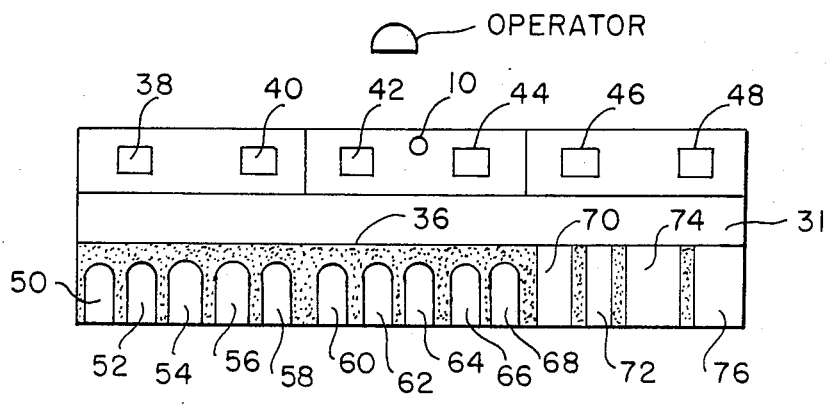
FIG. 2 is a schematic top diagram of the apparatus according to the invention illustrating the selector keys and the finger positioning assembly.

In FIG. 2, reference numerals 38, 40, 42, 44, 46, and 48 denote illuminating selector keys; 50, 52, 54, 56 and 58 denote concave-convex lenses to position the thumb, little, ring, middle and index fingers of the left hand, respectively; 60, 62, 64, 66 and 68 denote concave-convex lenses to position the thumb, index, middle, ring and little fingers of the the right hand, respectively; 70 and 72 denote plane lenses to position the left and right thumb, respectively; 74 and 76 denote plane lenses to position the left four fingers and the right four fingers, respectively; and 10 denotes a red light indicator.

Figure 3:
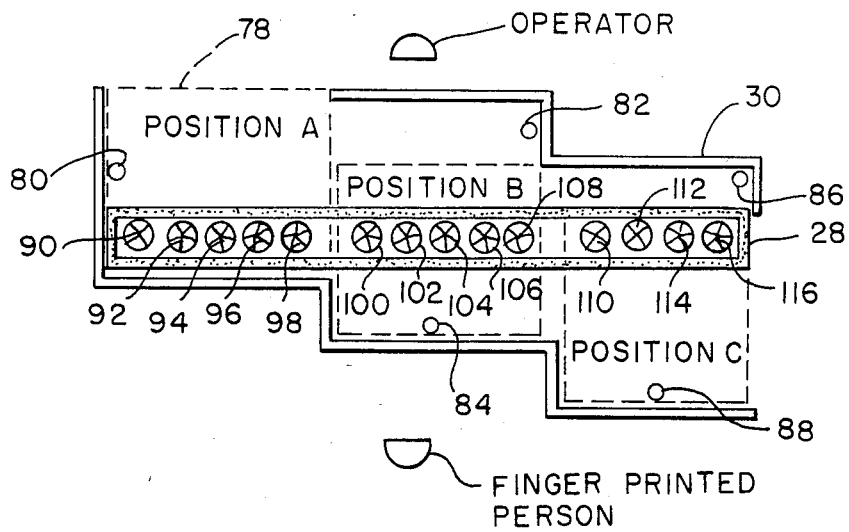
FIG. 3 is a schematic top section of the apparatus according to the invention illustrating the shutter assembly, the film chamber and various positions of the film chart during the fingerprinting operation.

In FIG. 3, reference numeral 78 denotes a film chart; 80, 82, 84, 86, and 88 denote electronic sensors; 90, 92, 94, 96, 98, 100, 102, 104, 106, 108, 110, 112, 114, and 116 denote shutters in the shutter assembly 28.

In an embodiment of the present invention, the camera 20, shown in FIG. 1 receives fingerprint images from the lenses in the fingers positioning assembly 36. These images enter through lens 24. The fingers positioned on assembly 36 receive illumination from light source 34 located inside the system. The images are projected on the corresponding shutters in the shutter assembly 28. At the command of the operator the corresponding shutters open and the images enter the film chamber 30 to be recorded on the film chart 78, which is positioned properly inside chamber 30. After the last images are recorded on chart 78 it is released outside the system ready for use. Now a new film chart 78 is fed into chamber 30 from the film feeder assembly 32. If the film feeder assembly 32 is empty, the sensor 80 will activate the red light indicator 10 announcing to the operator that the apparatus needs another film chart pack.

In FIG. 4, the film chart 78 is divided in 14 zones. Reference numerals 118, 120, 122, 124, and 126 denote the zones to record fingerprint images pertaining to the thumb, and the little, ring, middle and index fingers of the left hand, respectively; 128, 130, 132, 134, and 136 denote the zones to record fingerprint images pertaining to the thumb and the index, middle, ring, and little fingers of the right hand; 138 and 140 denote the zones to record fingerprint images pertaining to the left and right thumb, respectively; and 142 and 144 denote the zones to record fingerprint images of the four fingers of the left and right hand, respectively.

Referring now to FIGS. 2, 3, and 4, the fingerprinted person positions his left thumb on lens 50 of the assembly 36. At this time the selector key 38 is the only one illuminated and the film chart 78 is in position A on chamber 30. When the operator pushes selector key 38, shutter 98 opens and the image of the left thumb is recorded on zone 118 of the film chart 78. Selector key 38 turns off and selector key 40 now illuminates. Afterward, the person positions the four fingers of his left hand on lenses 52, 54, 56, and 58. At this particular time, the film chart is still in position A on chamber 30. When the operator pushes selector key 40, the shutters 96, 94, 92, and 90 open simultaneously and the images of the little, ring, middle, and index fingers projected on shutters 96, 94, 92, and 90, respectively, are now recorded on zones 120, 122, 124, and 126, respectively. Now the chart 78 moves to the right until it touches sensor 82. At this time sensor 82 sends a signal so that chart 78 moves to the front until it touches sensor 84. Then this sensor sends a signal to illuminate selector key 42 turning off selector key 40.

Chart 78 is now on position B ready for the next recording. The person now positions the right thumb on lens 60. When the operator pushes selector key 42, shutter 108 opens and the image of the right thumb is recorded on zone 128 of the chart 78. Selector key 42 turns off and selector key 44 now illuminates. Then the person positions the four fingers of his right hand on lenses 62, 64, 66, and 68. At this time, the chart 78 is still on position B on chamber 30. When the operator pushes selector key 44, the shutters 106, 104, 102, and 100 open simultaneously and the images of the index, middle, ring, and little finger projected on shutters 106, 104, 102, and 100, respectively, are now recorded on zones 130, 132, 134, and 136 of Chart 78, respectively. Now chart 78 moves to the right until it touches sensor 86. At this time sensor 86 sends a signal so that chart 78 moves to the front until it touches sensor 88. This sensor sends a signal to illuminate selector key 46 turning off selector key 44. Now chart 78 is on position C ready for next recordings. The person positions the left thumb on lens 70 and the right thumb on lens 72. When the operator pushes selector key 46, shutters 116 and 114 open simultaneously and the images of the left and the right thumbs projected on shutters 116 and 114, respectively, are recorded on zones 138 and 140 of chart 78, respectively. Selector key 46 turns off and selector key 48 illuminates. Now the person positions the four fingers of the left hand on lens 74 and the four fingers of the right hand on lens 76. At this particular time chart 78 is still on position C on Chamber 30. When the operator pushes key 48, the shutters 112 and 110 open simultaneously and the images of the left four fingers and the right four fingers projected on shutters 112 and 110, respectively, are recorded on zones 142 and 144 of chart 78, respectively. At this time, chart 78 is released out of the system and is ready to be used, key 48 is turned off, another chart is fed on position A and key 38 is illuminated again. Now the apparatus is ready for the next person to be fingerprinted.

Referring to FIG. 5, the camera 20 has approximately the same width as one third of the width of chart 78, and the same width of the shutters assembly 28. Also, the finger positioning assembly 36, the lens 24, the camera 20, and the shutter assembly 28 are all aligned on the same axis. This is an important consideration for an accurate image recording. The exterior enclosures of the apparatus must accommodate the film chamber 30.

In FIG. 6, a concave-convex lens is illustrated.

Figure 7:
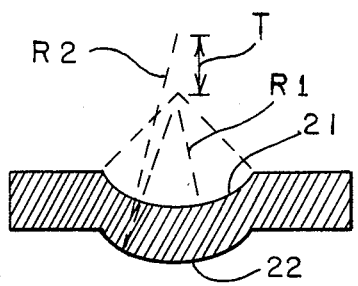
FIG. 7 is a diagramatic cross section of the concave-convex lens according to the invention.

In FIG. 7, a side view of the concave-convex lens is illustrated. A finger or thumb is positioned on the concave cylindrical surface 21 of this lens with a radii R1 as shown in FIG. 7. The convex cylindrical surface 22 has a radii R2. The distance T between radios may be 7/32", however, it may be reduced to an acceptable mechanical strength of the lens. Also, the ratio R1/R2 may be adjusted depending on the refractive index of the material used on any embodiment. Lenses 50, 52, 54, 56, 58 60, 62, 64, 66, and 68 are concave-convex lenses. Lenses 70, 72, 74, and 76 are flat or plane lenses.

Figure 8:
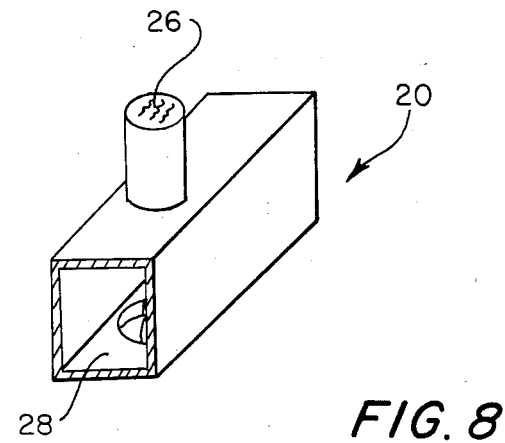
FIG. 8 is a fragmented perspective section of a camera according to the invention showing the inside of the camera with the shutter assembly.

In FIG. 8, the inside part of camera 20 is illustrated. The shutters assembly 28 constitutes the lower part of this camera. The entire camera 20 is attached to the film chamber 30.

Figure 9:
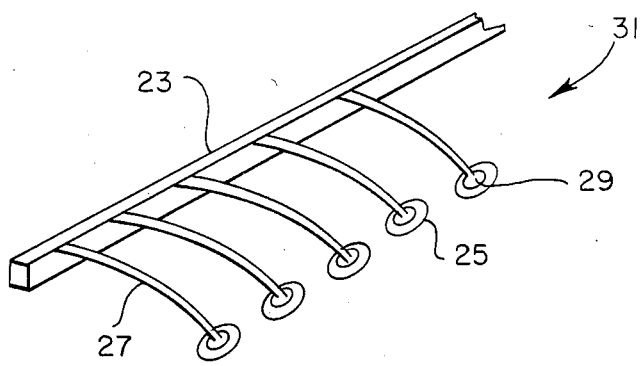
FIG. 9 is a perspective schematic diagram of the lens cleaning assembly according to the invention.

A fingerprinted person who positions the fingers on a lens surface stains the same by impressing ridge marks on said surface. This affects the recording accuracy of the next fingerprinting operation. To prevent this problem, the finger positioning lenses are cleaned automatically after each fingerprinting operation. A cleaning assembly 31 attached to the apparatus is provided, as shown in FIG. 9. This assembly comprises a plurality of cleaning pads 25, one for each lens, a plurality of tension bars 27, each one connecting at pad 25 at one end, and a supporting bar 23 holding the other end of all bars 27. The connection between pad 25 and tension bar 27 is a pivot joint 29. In this way, the pad 25 will adjust to the surface variations of the lenses to be cleaned. This assembly 31 will also include means for pushing bar 23 toward the lenses and means for pulling bar 23 toward its original position. This lens cleaning operation is performed automatically by the apparatus after chart 78 is released out of the apparatus.

It will thus be seen that the objects set forth above, and those made apparent by the preceeding description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. Apparatus to photocopy fingerprints, which comprises:
    a first lens for converting a curved image of a fingerprint to a flat image;
    means for illuminating said first lens so that the flat image is transmitted therefrom;
    a second lens coaxially related with said first lens to receive and transmit the flat image therefrom to a dark medium;
    a shutter located in the dark medium and coaxially related with second lens to temporarily hold the flat image therefrom when said shutter is closed and to permit transmission of the flat image when said shutter is open; and
    a film position relative to said shutter to receive and record permanently the flat image when said shutter opens.

2. A fingerprint photocopying apparatus as recited in claim 1, wherein said first lens comprises a concave-convex lens having a concave cylindrical surface and a convex cylindrical surface located at opposite sides of said lens, and wherein said first lens generates a fingerprint image of a finger positioned in the cylindrical concave surface.

3. A fingerprint photocopying apparatus as recited in claim 1, wherein said illuminating means comprises a source located inside the apparatus.

4. A fingerprint photocopying apparatus as recited in claim 1, further compressing means for controlling said shutter opening so the flat image transmitted from said first lens is recorded on said film.

5. A fingerprint photocopying apparatus as recited on claim 1, further comprising means for moving said film inside a dark medium to a position relative to said shutter.

6. A fingerprint photocopying apparatus as recited in claim 2, wherein said convex-concave lens is a glass lens with cylindrical symmetry and radii proportional to the refractive index of glass.

7. A fingerprint photocopying apparatus as recited in claim 5, wherein said film moving means comprises a dark chamber, in connection with said shutter, in which said film is positioned and later released when the flat image is recorded therein.

8. A fingerprint photocopying apparatus as recited in claim 1, wherein said second lens comprises a macrolens.

9. A fingerprint photocopying apparatus as recited in claim 2, wherein said convex-concave lens is a plastic lens with cylindrical symmetry and radii proportional to the refracting index of the plastic material.

10. Apparatus to photocopy fingerprints, which comprises:
    a plurality of first lenses for converting curved images of fingerprints to flat images;
    means for illuminating said first lenses so that a group of fingerprint images are transmitted therefrom;
    a second lens coaxially related with said first lenses to receive and transmit said group of flat images therefrom to a dark medium;
    a plurality of shutters located in the dark medium and coaxially related with said second lenses to temporarily hold said group of flat images therefrom when said shutters are closed and to permit transmission of said group of flat images when said shutters are open;
    a film moving to positions relative with said shutters to receive and record permanently said group of flat images when said shutters open; and means for controlling said shutters opening and said film positioning so that said group of flat images is recorded in a zone of said film.

11. A fingerprint photocopying apparatus as recited in claim 10, further comprising means for moving said film inside a dark medium to various positions relative with said shutters in accordance with said controlling means.

12. A fingerprint photocopying apparatus as recited in claim 11, further comprising:
    means for feeding said film into said apparatus;
    means for releasing said film from said apparatus; and
    means for cleaning said first lenses after said film is released.

13. A fingerprint photocopying apparatus as recited in claim 10, wherein said film is divided in fourteen zones.

* * * * *